(12) United States Patent
Dull et al.

(10) Patent No.: US 6,441,007 B1
(45) Date of Patent: Aug. 27, 2002

(54) PHARMACEUTICAL COMPOSITIONS AND METHODS FOR USE

(75) Inventors: Gary Maurice Dull, Lewisville; Grayland Page Dobson; Jared Miller Wagner, both of Winston-Salem, all of NC (US)

(73) Assignee: Targacept, Inc., Winston-Salem, NC (US)

( * ) Notice: Subject to any disclaimer, the term of this patent is extended or adjusted under 35 U.S.C. 154(b) by 0 days.

(21) Appl. No.: 09/628,995

(22) Filed: Jul. 31, 2000

Related U.S. Application Data

(63) Continuation of application No. 09/054,130, filed on Apr. 2, 1998, now abandoned.

(51) Int. Cl.$^7$ .................. A61K 31/44; C07D 213/63
(52) U.S. Cl. .................. 514/351; 546/300; 546/303
(58) Field of Search .................. 546/300, 303; 514/351

(56) References Cited

U.S. PATENT DOCUMENTS

| | | | |
|---|---|---|---|
| 4,599,336 A | 7/1986 | Carson et al. | |
| 4,927,838 A | 5/1990 | Guthrie et al. | |
| 5,212,188 A | 5/1993 | Caldwell et al. | |
| 5,585,388 A | 12/1996 | Cosford et al. | |
| 5,597,919 A | 1/1997 | Dull et al. | |
| 5,604,231 A | 2/1997 | Smith et al. | |
| 5,616,707 A | 4/1997 | Crooks et al. | |
| 5,616,716 A | 4/1997 | Dull et al. | |
| 5,629,325 A | 5/1997 | Lin et al. | |
| 5,663,194 A | 9/1997 | Mewshaw | |
| 5,663,356 A | 9/1997 | Ruecroft et al. | |
| 5,686,473 A | 11/1997 | Cosford et al. | 514/357 |
| 5,726,316 A | 3/1998 | Crooks et al. | |
| 5,731,314 A | 3/1998 | Bencherif et al. | |
| 5,736,560 A | 4/1998 | Cosford et al. | 514/343 |
| 5,811,442 A | 9/1998 | Bencherif et al. | |
| 5,824,692 A | 10/1998 | Lippiello et al. | |
| 5,852,041 A | 12/1998 | Cosford et al. | 514/351 |
| 5,861,423 A | 1/1999 | Caldwell et al. | |
| 5,885,998 A | 3/1999 | Bencherif et al. | 514/256 |

FOREIGN PATENT DOCUMENTS

| | | | |
|---|---|---|---|
| EP | 0 142 057 | 10/1984 | |
| EP | 0 559 413 A1 | 9/1993 | .......... A61K/31/465 |
| EP | 0 571 139 A1 | 11/1993 | .......... A61K/31/44 |
| EP | 0 230 035 | 10/1994 | |
| JP | 63264466 | 11/1988 | |
| WO | WO94/08992 | 4/1994 | .......... C07D/401/12 |
| WO | 95/12612 | 5/1995 | |
| WO | WO96/31475 | 10/1996 | .......... C07D/213/38 |
| WO | WO96/40682 | 12/1996 | .......... C07D/401/12 |
| WO | WO97/19059 | 5/1997 | .......... C07D/207/08 |
| WO | WO97/40011 | 10/1997 | .......... C07D/213/38 |
| WO | 97/42205 | 11/1997 | |
| WO | 98/25920 | 6/1998 | |
| WO | WO99/51216 | 10/1999 | .......... A61K/31/00 |
| WO | WO00/62767 | 10/2000 | .......... A61K/31/00 |
| WO | WO00/75110 | 12/2000 | .......... C07D/213/74 |

OTHER PUBLICATIONS

US 6,166,047, 12/2000, Dull et al. (withdrawn)*
Grail et al., "Derivatives of Dimethylamineothanol and Dimethylaminoethylamine,"60 The Journal of the American Chemical Society, vol. LXXIV, Jan.–Mar., 1952, pp. 1313–1315.
Mutai et al., "Photocyclization in 3–[ω–(Anilino)Alkoxy] Nitrobenzenes," Chemistry Letters, 1978, pp. 931–932.
Bremner et al., "Synthesis of 5–Aryl–1,4–benzoxazepine and 6–Phenyl–2H–1,5–benzoxazocine Derivatives," Aust. J. Chem, 1984, 37, pp. 129–141.
Tilley et al., "N–(Heterocyclic alkyl)pyrido[2,1–b] quinazoline–8–carboxamides as Orally Active Antiallergy Agents," J. Med. Chem., 1987, 30, pp. 185–193.
Guthrie et al., "Pentadienyl Carboxamide Derivatives as Antagonists of Platelet–Activating Factor," J. Med. Chem, 1989, 32, pp. 1820–1835.
Mitani et al., "Novel Phenoxylalkylamine Derivatives. II. Synthesis and Ca$^{2+}$–Antagonistic Activities of χ–Alkyl–χ–[(phenoxypropylamino)propyl]–benzeneacetonitrile Derivatives," Chem. Pharm. Bull., vol. 36, No. 1, 1988, pp. 373–385.
Abreo et al., "Novel 3–Pyridyl Ethers with Subnanomolar Affinity for Central Neuronal Nicotinic Acetylcholine Receptors," *J. Med. Chem.*, 39: 817–825 (1996).
Bannon et al., "Broad–Spectrum, Non–Opiod Analgesic Activity by Selective Modulation of Neuronal Nicotinic Acetylcholine Receptors," *Science*, 279: 77–81 (Jan. 2, 1998).
Elliott et al., "2–(Aryloxymethyl) Azacyclic Analogues as Novel Nicotinic Acetylcholine Receptor (nAChR) Ligands," *Bioorganic & Medicinal Chemistry Letters*, 6(19): 2283–2288 (1996).
Elliott et al., "Novel 2–(2'–Furo[3,2–b]Pyridinyl) Pyrrolidines: Potent Neuronal Nicotinic Acetylcholine Receptor Ligands," *Bioorganic & Medicinal Chemistry Letter*, 7(21): 2703–2708 (1997).
Holladay et al., "Identification and Initial Structure–Activity Relationships of (R)–5–(2–Azetidinylmethoxy)–2–chloropyridine (ABT–594), a Potent, Orally Active, Non–Opiate Analgesic Agent Acting via Neuronal Nicotinic Acetylcholine Receptors," *Journal of Medicinal Chemistry*, 41 (4): 407–412 (Feb. 12, 1998).

(List continued on next page.)

*Primary Examiner*—Charanjit S. Aulakh
(74) *Attorney, Agent, or Firm*—Womble Carlyle Sandridge & Rice, PLLC

(57) ABSTRACT

Patients susceptible to or suffering from conditions and disorders, such as central nervous system disorders, are treated by administering to a patient in need thereof aryloxyalkylamines, including pyridyloxylalkylamines and phenoxyalkylamines, such as (3-(3-pyridyloxy)propyl) methylamine and (3-(5-bromo(3-pyridyloxy))propyl) methylamine.

42 Claims, No Drawings-

OTHER PUBLICATIONS

Lippiello, P. et al., JPET, vol. 279. No. 3, pp. 1422–1429 (1996).
Bencherif, M. et al., JPET, vol. 279, No. 3, pp. 1413–1421 (1996).
Tilley, J. W. et al., *J. Med. Chem.*, vol. 30, pp. 185–193 (1987).
Guthrie, R. W. et al., *J. Med. Chem.*, vol. 32, pp. 1820–1835 (1989).
Unangst, P. C. et al., *J. Med. Chem.*, vol. 40, pp. 4026–4029 (1997).
Iwakura, Y. et al., Bulletin of the Chemical Society of Japan, vol. 43, pp.2531–2535 (1970).
Schaeffer, J. C. et al., *J. of Pharm. Sciences*, vol. 65(1), pp. 122–126 (1976).
Arora S. K. et al., *J. Med. Chem.* vol. 30, pp. 918–924 (1987).
Buschauer, A., *Eur. J. Med. Chem.*, vol. 23, pp. 1–6 (1988).
Kawase, M. et al., *Biochemical Pharmacology*, vol. 31, No. 18, pp. 2983–2988 (1982).
Lever, Jr., O.W. et al., *J. Med. Chem.*, vol. 28, pp. 1870–1874 (1985).
Pierson, M. E. et al., *J. Med. Chem.*, vol. 32, pp. 859–863 (1989).
Ismaiel, A. M. et al., *J. Med. Chem.*, 40 (26), pp. 4415–4419 (1997).
Brenner J. B. et al., *aust J. Chem.*, vol. 37, pp. 129–141 (1984).
Mitanl, K. et al., Chem. Pharm. Bull., vol. 36(10), pp. 4103–4120 (1988).
Mitanl, K. et al., Chem. Pharm. Bull., vol. 36(1), pp. 373–385 (1988).
Brenner, J. B. et al., *Aust. J. Chem.*, vol. 37, pp. 129–141 (1984).
Wubbels, G. G. et al., *J. Org. Chem.*, vol. 50, pp. 4499–4504 (1985).
Wubbels, G. G. et al., Tetrahedron Letters, vol. 30, No. 47, pp. 6477–6480 (1989).
Wubbels, G. G. et al., *J. Org. Chem.*, vol. 60, pp. 2960–2961 (1995).
Mewshaw, R. E. et al., *J. Medicinal Chem.*, vol. 40, No. 26, pp. 4235–4256 (1997).
Mutai, K. et al., Chemistry Letters, pp. 931–932 (1978).

\* cited by examiner

PHARMACEUTICAL COMPOSITIONS AND METHODS FOR USE

This is a continuation application claiming the benefit of application Ser. No. 09/054,130 filed Apr. 2, 1998, now abandoned, the disclosure of which is incorporated herein by reference.

BACKGROUND OF THE INVENTION

The present invention relates to pharmaceutical compositions, and particularly pharmaceutical compositions incorporating compounds that are capable of affecting nicotinic cholinergic receptors. More particularly, the present invention relates to compounds capable of activating nicotinic cholinergic receptors, for example, as agonists of specific nicotinic receptor subtypes. The present invention also relates to methods for treating a wide variety of conditions and disorders, and particularly conditions and disorders associated with dysfunction of the central and autonomic nervous systems.

Nicotine has been proposed to have a number of pharmacological effects. See, for example, Pullan et al. *N. Engl. J. Med.* 330:811–815 (1994). Certain of those effects may be related to effects upon neurotransmitter release. See for example, Sjak-shie et al., *Brain Res.* 624:295 (1993), where neuroprotective effects of nicotine are proposed. Release of acetylcholine and dopamine by neurons upon administration of nicotine has been reported by Rowell et al., *J. Neurochem.* 43:1593 (1984); Rapier et al., *J. Neurochem.* 50:1123 (1988); Sandor et al., *Brain Res.* 567:313 (1991) and Vizi, *Br. J. Pharmacol.* 47:765 (1973). Release of norepinephrine by neurons upon administration of nicotine has been reported by Hall et al., *Biochem. Pharmacol.* 21:1829 (1972). Release of serotonin by neurons upon administration of nicotine has been reported by Hery et al., *Arch. Int. Pharmacodyn. Ther.* 296:91 (1977). Release of glutamate by neurons upon administration of nicotine has been reported by Toth et al., *Neurochem Res.* 17:265 (1992). In addition, nicotine reportedly potentiates the pharmacological behavior of certain pharmaceutical compositions used for the treatment of certain disorders. See, Sanberg et al., *Pharmacol. Biochem. & Behavior* 46:303 (1993); Harsing et al., *J. Neurochem.* 59:48 (1993) and Hughes, *Proceedings from Intl. Symp. Nic.* S40 (1994). Furthermore, various other beneficial pharmacological effects of nicotine have been proposed. See, Decina et al., *Biol. Psychiatry* 28:502 (1990); Wagner et al., *Pharmacopsychiatry* 21:301 (1988); Pomerleau et al., *Addictive Behaviors* 9:265 (1984); Onaivi et al., *Life Sci.* 54(3):193 (1994); Tripathi et al., JPET221: 91–96 (1982) and Hamon, *Trends in Pharmacol. Res.* 15:36.

Various nicotinic compounds have been reported as being useful for treating a wide variety of conditions and disorders. See, for example, Williams et al. *DN&P* 7(4):205–227 (1994), Arneric et al., *CNS Drug Rev.* 1(1):1–26 (1995), Arneric et al., *Exp. Opin. Invest. Drugs* 5(1):79–100 (1996), Bencherif et al., *JPET* 279:1413 (1996), Lippiello et al., *JPET* 279:1422 (1996), Damaj et al., *Neuroscience* (1997), Holladay et al., *J. Med. Chem* 40(28): 4169–4194 (1997), Bannon et al., *Science* 279: 77–80 (1998), PCT WO 94/08992, PCT WO 96/31475, and U.S. Pat. Nos. 5,583,140 to Bencherif et al., U.S. Pat. No. 5,597,919 to Dull et al., and U.S. Pat. No. 5,604,231 to Smith et al. Nicotinic compounds are reported as being particularly useful for treating a wide variety of Central Nervous System (CNS) disorders.

CNS disorders are a type of neurological disorder. CNS disorders can be drug induced; can be attributed to genetic predisposition, infection or trauma; or can be of unknown etiology. CNS disorders comprise neuropsychiatric disorders, neurological diseases and mental illnesses; and include neurodegenerative diseases, behavioral disorders, cognitive disorders and cognitive affective disorders. There are several CNS disorders whose clinical manifestations have been attributed to CNS dysfunction (i.e., disorders resulting from inappropriate levels of neurotransmitter release, inappropriate properties of neurotransmitter receptors, and/or inappropriate interaction between neurotransmitters and neurotransmitter receptors). Several CNS disorders can be attributed to a cholinergic deficiency, a dopaminergic deficiency, an adrenergic deficiency and/or a serotonergic deficiency. CNS disorders of relatively common occurrence include presenile dementia (early onset Alzheimer's disease), senile dementia (dementia of the Alzheimer's type), Parkinsonism including Parkinson's disease, Huntington's chorea, tardive dyskinesia, hyperkinesia, mania, attention deficit disorder, anxiety, dyslexia, schizophrenia and Teurette's syndrome.

It would be desirable to provide a useful method for the prevention and treatment of a condition or disorder by administering a nicotinic compound to a patient susceptible to or suffering from such a condition or disorder. It would be highly beneficial to provide individuals suffering from certain disorders (e.g., CNS diseases) with interruption of the symptoms of those disorders by the administration of a pharmaceutical composition containing an active ingredient having nicotinic pharmacology and which has a beneficial effect (e.g., upon the functioning of the CNS), but which does not provide any significant associated side effects. It would be highly desirable to provide a pharmaceutical composition incorporating a compound which interacts with nicotinic receptors, such as those which have the potential to effect the functioning of the CNS, but which compound when employed in an amount sufficient to effect the functioning of the CNS, does not significantly effect those receptor subtypes which have the potential to induce undesirable side effects (e.g., appreciable activity at skeletal muscle sites).

SUMMARY OF THE INVENTION

The present invention relates aryloxyalkylamines, including pyridyloxyalkylamines and phenoxyalkylamines, such as (3-(3-pyridyloxy)propyl)methylamine and (3-(5-bromo (3-pyridyloxy))propyl)methylamine.

The present invention also relates to methods for the prevention or treatment of a wide variety of conditions or disorders, and particularly those disorders characterized by disfunction of nicotinic cholinergic neurotransmission including disorders involving neuromodulation of neurotransmitter release, such as dopamine release. The present invention also relates to methods for the prevention or treatment of disorders, such as central nervous system (CNS) disorders, which are characterized by an alteration in normal neurotransmitter release. The present invention also relates to methods for the treatment of certain conditions (e.g., a method for alleviating pain). The methods involve administering to a subject an effective amount of a compound of the present invention.

The present invention, in another aspect, relates to a pharmaceutical composition comprising an effective amount of a compound of the present invention. Such a pharmaceutical composition incorporates a compound which, when employed in effective amounts, has the capability of interacting with relevant nicotinic receptor sites of a subject, and hence has the capability of acting as a therapeutic agent in the prevention or treatment of a wide variety of conditions and disorders, particularly those disorders characterized by an alteration in normal neurotransmitter release. Preferred pharmaceutical compositions comprise compounds of the present invention.

The pharmaceutical compositions of the present invention are useful for the prevention and treatment of disorders, such as CNS disorders, which are characterized by an alteration in normal neurotransmitter release. The pharmaceutical compositions provide therapeutic benefit to individuals suffering from such disorders and exhibiting clinical manifestations of such disorders in that the compounds within those compositions, when employed in effective amounts, have the potential to (i) exhibit nicotinic pharmacology and affect relevant nicotinic receptors sites (e.g., act as a pharmacological agonist to activate nicotinic receptors), and (ii) elicit neurotransmitter secretion, and hence prevent and suppress the symptoms associated with those diseases. In addition, the compounds are expected to have the potential to (i) increase the number of nicotinic cholinergic receptors of the brain of the patient, (ii) exhibit neuroprotective effects and (iii) when employed in effective amounts do not cause appreciable adverse side effects (e.g., significant increases in blood pressure and heart rate, significant negative effects upon the gastrointestinal tract, and significant effects upon skeletal muscle). The pharmaceutical compositions of the present invention are believed to be safe and effective with regards to prevention and treatment of a wide variety of conditions and disorders.

The foregoing and other aspects of the present invention are explained in detail in the detailed description and examples set forth below.

DETAILED DESCRIPTION OF THE INVENTION

The compounds of the present invention include compounds of the formula I:

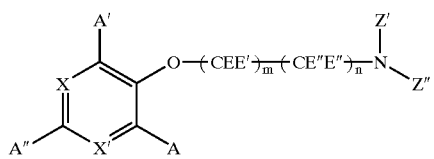

where each of X and X' are individually nitrogen or carbon bonded to a substituent species characterized as having a sigma m value greater than 0, often greater than 0.1, and generally greater than 0.2, and even greater than 0.3; less than 0 and generally less than −0.1; or 0; as determined in accordance with Hansch et al., *Chem. Rev.* 91:165 (1991); m is an integer and n is an integer such that the sum of m plus n is 1, 2, 3, 4, 5, 6, 7, or 8, preferably is 1, 2, or 3, and most preferably is 2 or 3; E, E', E" and E''' individually represent hydrogen or lower alkyl (e.g., straight chain or branched alkyl including $C_1$–$C_8$, preferably $C_1$–$C_5$, such as methyl, ethyl, or isopropyl) or halo substituted lower alkyl (e.g., straight chain or branched alkyl including $C_1$–$C_8$, preferably $C_1$–$C_5$, such as trifluoromethyl or trichloromethyl), but preferably are H; and Z' and Z" individually represent hydrogen or lower alkyl (e.g., straight chain or branched alkyl including $C_1$–$C_8$, preferably $C_1$–$C_5$, such as methyl, ethyl, or isopropyl), and preferably at least one of Z' any Z" is hydrogen, and most preferably Z' is hydrogen and Z" is methyl; alternatively Z' is hydrogen and Z" represents a ring structure (cycloalkyl or aromatic), such as cyclopropyl, cyclobutyl, cyclopentyl, cyclohexyl, cycloheptyl, adamantyl, quinuclidinyl, pyridinyl, quinolinyl, pyrimidinyl, phenyl, benzyl (where any of the foregoing can be suitably substituted with at least one substituent group, such as alkyl, halo, or amino substituents); alternatively Z', Z", and the associated nitrogen atom can form a ring structure such as aziridinyl, azetidinyl, pyrollidinyl, piperidinyl, piperazinyl, or morpholinyl. More specifically, X and X' include N, C—H, C—F, C—Cl, C—Br, C—I, C—R', C—NR'R", C—CF$_3$, C—OH, C—CN, C—NO$_2$, C—C$_2$R', C—SH, C—SCH$_3$, C—N$_3$, C—SO$_2$CH$_3$, C—OR', C—SR', C—C(=O)NR'R", C—NR'C(=O)R', C—C(=O)R', C—C(=O)OR', C(CH$_2$)$_q$OR', C—OC(=O)R', COC(=O)NR'R" and C—NR'C(=O)OR' where R' and R" are individually hydrogen or lower alkyl (e.g., $C_1$–$C_{10}$ alkyl, preferably $C_1$–$C_5$ alkyl, and more preferably methyl, ethyl, isopropyl or isobutyl), an aromatic group-containing species or a substituted aromatic group-containing species, and q is an integer from 1 to 6. R' and R" can be straight chain or branched alkyl, or R' and R" can form a cycloalkyl functionality (e.g., cyclopropyl cyclobutyl, cyclopentyl, cyclohexyl, cycloheptyl, adamantyl, and quinuclidinyl). Representative aromatic group-containing species include pyridinyl, quinolinyl, pyrimidinyl, phenyl, and benzyl (where any of the foregoing can be suitably substituted with at least one substituent group, such as alkyl, halo, or amino substituents). Other representative aromatic ring systems are set forth in Gibson et *J. Med. Chem.* 39:4065 (1996). When X and X' represent a carbon atom bonded to a substituent species, that substituent species often has a sigma m value which is between about −0.3 and about 0.75, and frequently between about −0.25 and about 0.6. In certain circumstances the substituent species is characterized as having a sigma m value not equal to 0. A, A' and A" individually represent those species described as substituent species to the aromatic carbon atom previously described for X and X'; and usually include hydrogen, halo (e.g., F, Cl, Br, or I), alkyl (e.g., lower straight chain or branched $C_{1-8}$ alkyl, but preferably methyl or ethyl), or NX'X''' where X" and X''' are individually hydrogen or lower alkyl, including $C_1$–$C_8$, preferably $C_1$–$C_5$ alkyl. In addition, it is highly preferred that A is hydrogen, it is preferred that A' is hydrogen, and normally A" is hydrogen. Generally, both A and A' are hydrogen; sometimes A and A' are hydrogen, and A" is amino, methyl or ethyl; and often A, A' and A" are all hydrogen. Depending upon the identity and positioning of each individual E, E, E" and E''', certain compounds can be optically active. Typically, the selection of E, E', E" and E''' is such that up to about 4, and frequently up to 3, and usually 0, 1 or 2, of the substituents designated as E, E', E" and E''' are non-hydrogen substituents (i.e., substituents such as lower alkyl or halo-substituted lower alkyl). Typically, X is CH, CBr or COR. Most preferably, X' is nitrogen.

One representative compound is (3-(3-pyridyloxy)propyl) methylamine, for which X is CH, X' is N, n is 0, m is 3, A, A', A", E, E' and Z' are each H, and Z" is methyl. One representative compound is (3-(3-pyridyloxy)propyl)amine, for which X is CH, X' is N, n is 0, m is 3, and A, A', A", E, E', Z' and Z" are each H. One representative compound is (3-(5-bromo-(3-pyridyloxy)propyl)methylamine, for which X is C—Br, X' is N, n is 0, m is 3, A, A', A", E, E' and Z' are each H, and Z" is methyl. One representative compound is (1-methyl-3-(3-pyridyloxy)propyl)methylamine, for which X is CH, X' is N, n is 1, m is 2, A, A', A", E, E', E" and Z' are each H, and E''' and Z" are methyl. One representative compound is (3-(5-ethoxy-(3-pyridyloxy)propyl)

methylamine, for which X is C—OCH$_2$CH$_3$, X' is N, n is 0, m is 3, A, A', A", E, E' and Z' are each H, and Z" is methyl. One representative compound is (3-(6-methyl-(3-pyridyloxy)propyl)methylamine, for which X is CH, X' is N, n is 0, m is 3, A, A', E, E' and Z' are each H, and A" and Z" each are methyl. One representative compound is (3-(5-chloro-(3-pyridyloxy)propyl)methylamine, for which X is C—Cl, X' is N, n is 0, m is 3,A, A', A", E, E' and Z' are each H, and Z" is methyl. One representative compound is (3-(2-bromo(3-pyridyloxy)propyl)methylamine, for which X is CH, X' is N, n is 0, m is 3, A is Br, A', A", E, E' and Z' are each H, and Z" is methyl. One representative compound is (1-methyl-3-(5-methoxy-(3-pyridyloxy)propyl)) methylamine, for which X is C—OCH$_3$, X' is N, n is 1, m is 2, A, A', A", E, E', E" and Z' are each H, and E'" and Z" are each methyl. One representative compound is (4-(3-pyridyloxy)butyl))methylamine, for which X is CH, X' is N, n is 0, m is 4, A, A', A", E, E', and Z' are each H, and Z" is methyl. One representative example is (3-phenoxypropyl) methylamine, for which X and X' are each CH, n is 0, m is 3, A, A', A", E, E' and Z' are each H, and Z" is methyl. One representative example is (3-(3-aminophenoxy)propyl) methylamine, for which X is CH, X' is C—NH$_2$, n is 0, m is 3, A, A', A", E, E' and Z' are each H, and Z" is methyl. One representative example is (3-(4-methoxyphenoxy)propyl) methylamine, for which X and X' are each CH, n is 0, m is 3, A, A', E, E' and Z' are each H, A" is OCH$_3$, and Z" is methyl.

The manner in which certain phenoxyalkylamine compounds of the present invention are provided can vary. Certain phenoxyalkylamine compounds can be prepared by the alkylation of phenol with a 1,3-dihalopropane, such as 1,3-dichloropropane, 1,3-dibromopropane, 1,3-diiodopropane, or 1-chloro-3-iodopropane, which are commercially available from Aldrich Chemical Company, in the presence of a base (e.g., sodium hydride) in dry N,N-dimethylformamide. The resulting 3-halo-1-phenoxypropane can be converted to a phenoxyalkylamine, such as methyl(3-phenoxypropyl)amine, by treatment with methylamine in a solvent, such as tetrahydrofuran or aqueous methanol. The manner in which certain 3-substituted-phenyl analogs of (3-phenoxypropyl)methylamine of the present invention can be synthetically prepared is analogous to that described for the preparation of methyl(3-phenoxypropyl)amine with the exception that 3-substituted-phenols are employed rather than phenol. In some instances, protecting groups may be employed when necessary. For example, one representative compound, (3-(3-aminophenoxy)propyl)methylamine can be prepared by the alkylation of an N-phthalamido-protected phenol, 2-(3-hydroxyphenyl)isoindoline-1,3-dione (prepared by treatment of 3-aminophenol with phthalic anhydride) with 1-chloro-3-iodopropane. The resulting intermediate, 2-(3-(3-chloropropoxy)-phenyl)isoindoline-1,3-dione can be converted to (3-(3-aminophenoxy)-propyl)methylamine by treatment with methanolic methylamine. The manner in which certain 4-substituted-phenyl analogs of methyl(3-phenoxypropyl)amine of the present invention can be synthetically prepared is analogous to that described for the preparation of methyl(3-phenoxypropyl)amine with the exception that 4-substituted-phenols are employed rather than phenol. For example, 4-methoxyphenol can be converted to (3-(4-methoxyphenoxy)propyl)methylamine.

The manner by which pyridyloxyalkylamine compounds of the present invention are provided can vary. Certain pyridyloxyalkylamine compounds can be prepared by the alkylation of 3-hydoxypyridine with a 1,3-dihalopropane, such as 1,3-dichloropropane, 1,3-dibromopropane, 1,3-diodopropane or 1-chloro-3-iodopropane, which are commercially available from Aldrich Chemical Company, in the presence of a base (e.g., sodium hydride) in dry N,N-dimethylformamide. The resulting 3-halo-1-(3-pyridyloxy) propane can be converted to a pyridyloxyalkylamine, such as (3-(3-pyridyloxy)propyl)methylamine, by treatment with methylamine in a solvent, such as tetrahydrofuran or aqueous methanol. One representative compound, (3-(3-pyridyloxy)propyl)methylamine is prepared by the reaction of 3-hydroxypyridine with 1.2 molar equivalents of 1-chloro-3-iodopropane and 1.6 molar equivalents of sodium hydride in dry N,N-dimethylformamide at ambient temperature. The resulting intermediate, 3-chloro-1-(3-pyridyloxy)propane, obtained in about 54% yield, is converted to (3-(3-pyridyloxy)propyl)methylamine in about 40% yield, by treatment with an excess (25 molar equivalents) of aqueous methylamine in methanol, assisted by heating. Certain pyridyloxyalkylamine compounds, such as (4-(3-pyridyloxy)-butyl)methylamine, can be prepared by alkylating 3-hydroxypyridine with a 1,4-dihalobutane, such as 1,4-diiodobutane, 1,4-dibromobutane, 1,4-dichlorobutane or 1-chloro-4-iodobutane, which are commercially available from Aldrich Chemical Company, in the presence of a base (e.g., sodium hydride) in N,N-dimethylformamide. The resulting 4-halo-1-(3-pyridyloxy)butane can be converted to a pyridyloxyalkylamine, such as (4-(3-pyridyloxy)butyl) methylamine, by treatment with methylamine in a solvent, such as tetrahydrofuran or aqueous methanol.

The manner by which certain 2-substituted-3-pyridyl analogs of (3-(3-pyridyloxy)propyl)methylamine and certain 6-substituted-3-pyridyl analogs of (3-(3-pyridyloxy)propyl) methylamine of the present invention can be synthetically prepared is analogous to that described for the preparation of (3-(3-pyridyloxy)-propyl)methylamine with the exception that 2-substituted-3-hydroxypyridines and 6-substituted-3-hydroxypyridines are employed rather than 3-hydroxypyridine. For example, using such methodology, commercially available 2-bromo-3-hydroxypyridine and 3-hydroxy-2-nitropyridine can be converted to 3-(2-bromo (3-pyridyloxy))propyl)methylamine and 3-(2-nitro(3-pyridyloxy))propyl)methylamine, respectively. Similarly, commercially available 3-hydroxy-6-methylpyridine can be converted to 3-(6-methyl(3-pyridyloxy))propyl) methylamine.

The manner by which certain 5-substituted-3-pyridyl analogs of (3-(3-pyridyloxy)propyl)methylamine of the present invention can be synthesized is analogous to that described for (3-(3-pyridyloxy)propyl)methylamine, with the exception that 5-substituted-3-hydroxypyridines are employed rather than 3-hydroxypyridine. For example, using such a methodology, 5-bromo-3-hydroxypyridine can be converted to the intermediate, 3-chloro-1-(5-bromo-3-pyridyloxy) propane, which is converted to 3-(5-bromo(3-pyridyloxy))-propyl)methylamine. 5-Bromo-3-hydroxypyridine can be prepared form 2-furfurylamine using the procedure described in U.S. Pat. No. 4,192,946 to Clauson-Kaas et al. the disclosure of which is incorporated herein by reference in its entirety. In a similar manner, 5-chloro-3-hydroxypyridine, which is commercially available from Aldrich Chemical Company, can be converted to 3-(5-chloro (3-pyridyloxy))propyl)methylamine. Similarly, 5-methoxy-3-hydroxypyridine, prepared according to the procedures set forth in Chen et al., *Heterocycles* 24(12): 3411 (1986), can be converted to 3-(5-methoxy(3-pyridyloxy))propyl) methylamine. Similarly, 5-ethoxy-3-hydroxypyridine can be converted to 3-(5-ethoxy(3-pyridyloxy))propyl)

methylamine. Similarly, 5-amino-3-hydroxypyridine, prepared according to the procedures set forth in Tamura et al., *Heterocycles* 15(2): 871 (1981), can be converted to 3-(5-amino(3-pyridyloxy))propyl)methylamine. In a similar manner, 3-hydroxy-5-trifluoromethylpyridine and 2-fluoro-5-hydroxy-3-methylpyridine, each prepared using methods set forth in PCT WO 96/40682, can be converted to 3-(5-trifluoromethyl(3-pyridyloxy))propyl)methylamine and 3-(5-fluoro-5-methyl(3-pyridyloxy))propyl)methylamine, respectively.

A number of 5-substituted analogs, such as (3-(5-substituted(3-pyridyloxy))propyl)methylamine, can be synthesized from 5-substituted 3-hydroxypyridines, which can be prepared from 5-amino-3-hydroxypyridine via a diazonium salt intermediate. For example, 5-amino-3-hydroxypyridine can be converted to 5-fluoro-3-hydroxypyridine, 5-chloro-3-hydroxypyridine, 5-bromo-3-hydroxypyridine, 5-iodo-3-hydroxypyridine or 5-cyano-3-hydroxypyridine, using the general techniques set forth in Zwart et al., *Recueil Trav. Chim. Pays-Bas* 74: 1062 (1955). Futhermore, 5-hydroxy-substituted analogs can be prepared from the reaction of the corresponding 5-diazonium salt intermediate with water. The 5-Fluoro-substituted analogs can be prepared from the reaction of the 5-diazonium salt intermediate with fluoroboric acid. 5-Chloro-substituted analogs can be prepared from the reaction of 5-amino-3-hydroxypyridine with sodium nitrite and hydrochloric acid in the presence of copper chloride. The 5-cyano-substituted analogs can be prepared from the reaction of the corresponding diazonium salt intermediate with potassium copper cyanide. The 5-amino-substituted analogs can be converted to the corresponding 5-nitro analogs by reaction with fuming sulfuric acid and peroxide according to the general techniques described in Morisawa, *J. Med. Chem.* 20: 129 (1977), for converting an amino pyridine to a nitropyridine.

Certain pyridyloxyalklylamines that possess a branched side chain, such as (1-methyl-3-(3-pyridyloxy)propyl)methylamine, can be prepared by alkylating 3-hydroxypyridine with a protected 3-hydroxy-1-halobutane, such as 3-[(tert-butyl)dimethylsilyloxy]-1-bromobutane (prepared according to the procedures set forth in Gerlach et al., *Helv. Chim. Acta.* 60(8): 2860 (1977)), thereby producing a (tert-butyl)dimethylsilyl protected 4-(3-pyridyloxy)butan-2-ol. The (tert-butyl)dimethylsilyl group can be removed by treatment with ammonium fluoride or aqueous acetic acid to give 4-(3-pyridyloxy)butan-2-ol. Mesylation or tosylation of that compound with methanesulfonyl chloride in triethylamine or p-toluenesulfonyl chloride in pyridine, followed by treatment with methylamine in tetrahydrofuran or aqueous methanol, provides a compound having a methyl branched side chain (e.g., (1-methyl-3-(3-pyridyloxy)propyl)methylamine).

Alternatively, pyridyloxyalkylamines possessing a branched side chain, such as (1-methyl-3-(3-pyridyloxy)propyl)methylamine, can be synthesized by alkylating 3-hydroxypyridine with a protected 1-iodo-3-butanone, namely 2-methyl-2-(2-iodoethyl)-1,3-dioxolane, with is prepared according to the procedures set forth in Stowell et al., *J. Org. Chem.* 48: 5381 (1983). The resulting ketal, 3-(2-(1-methyl-2,5-dioxolanyl)ethoxy)pyridine, can be protected by treatment with aqueous acetic acid or p-toluenesulfonic acid in methanol to yield 4-(3-pyridyloxy)butan-2-one. Reductive amination of the resulting ketone using methylamine and sodium cyanoborohydride according to the methodology set forth in Borch, *Org. Syn.* 52: 124 (1972) provides (1-methyl-3-(3-pyridyloxy)propyl)methylamine. Alternatively, the intermediate, 4-(3-pyridyloxy)butan-2-one, can be reduced with sodium borohydride to yield an alcohol, 4-(3-pyridyloxy)butan-2-ol. Mesylation or tosylation of that alcohol, followed by mesylation or tosylation displacement using methylamine, provides the branched chain pyridyloxyalkylamine, (1-methyl-3-(3-pyridyloxy)propyl)methylamine.

Chiral starting materials are available for the synthesis of the pure enantiomers of the branched chain pyridyloxyalkylamines, such a (1-methyl-3-(3-pyridyloxy)propyl)methylamine. One approach can be carried out using either methyl (R)-(−)-3-hydroxybutyrate or the (+)-enantiomer, (S)-(+)-3-hydroxybutyrate, both of which are available from Aldrich Chemical Company. For example, (R)-(−)-3-hydroxybutyrate can be converted to (R)-(−)-3-tetrahydropyranyloxybutyl bromide, using the procedures set forth in Yuasa et al., *J Chem. Soc., Perk. Trans.* 1(5): 465 (1996). Alkylation of 3-hyroxypyridine with (R)-(−)-3-tetrahydropyranyloxybutyl bromide using sodium hydride in N,N-dimethylformamide produces the tetrahydropyranyl ether of 4-(3-pyridyloxy)butan-2R-ol. Removal of the tetrahydropyranyl protecting group of that compound using p-toluenesulfonic acid monohydrate in methanol affords 4-(3-pyridyloxy)butan-2R-ol. The resulting chiral alcohol can be elaborated to the chiral pyridyloxyalkylamine, (1S-3-(3-pyridyloxy)propyl)methylamine using a two-step sequence involving tosylation and methylamine displacement of the intermediate tosylate. In a similar process, (S)-(+)-3-hydroxybutyrate can be converted to (S)-(+)-3-tetrahydropyranyloxybutyl bromide using the procedures set forth in Sakai et al., *Agric. Biol. Chem.* 50(6): 1621 (1986). This protected bromo alcohol can be converted to the corresponding chiral pyridyloxyalkylamine, methyl(1R-3-(3-pyridyloxy)propyl)amine, using a sequence involving alkylation of 3-hydroxypyridine, removal of the tetrahydropyranyl group, tosylation, and methylamine displacement of the intermediate tosylate.

The present invention relates to a method for providing prevention of a condition or disorder to a subject susceptible to such a condition or disorder, and for providing treatment to a subject suffering therefrom. For example, the method comprises administering to a patient an amount of a compound effective for providing some degree of prevention of the progression of a CNS disorder (i.e., provide protective effects), amelioration of the symptoms of a CNS disorder, and amelioration of the reoccurrence of a CNS disorder. The method involves administering an effective amount of a compound selected from the general formulae which are set forth hereinbefore. The present invention relates to a pharmaceutical composition incorporating a compound selected from the general formulae which are set forth hereinbefore. The compounds normally are not optically active. However, certain compounds can possess substituent groups of a character so that those compounds possess optical activity. Optically active compounds can be employed as racemic mixtures or as enantiomers. The compounds can be employed in a free base form or in a salt form (e.g., as pharmaceutically acceptable salts). Examples of suitable pharmaceutically acceptable salts include inorganic acid addition salts such as hydrochloride, hydrobromide, sulfate, phosphate, and nitrate; organic acid addition salts such as acetate, galactarate, propionate, succinate, lactate, glycolate, malate, tartrate, citrate, maleate, fumarate, methanesulfonate, p-toluenesulfonate, and ascorbate; salts with acidic amino acid such as aspartate and glutamate; alkali metal salts such as sodium salt and potassium salt; alkaline earth metal salts such as magnesium salt and calcium salt; ammonium salt; organic basic salts such as trimethylamine salt, triethylamine salt, pyridine salt, picoline salt, dicyclohexylamine salt, and N,N'-dibenzylethylenediamine salt; and salts with basic amino acid such as lysine salt and arginine salt. The salts may be in some cases hydrates or ethanol solvates.

Compounds of the present invention are useful for treating those types of conditions and disorders for which other types of nicotinic compounds have been proposed as therapeutics. See, for example, Williams et al. *DN&P* 7(4):205–227 (1994), Arneric et al., *CNS Drug Rev.* 1(1): 1–26 (1995), Arneric et al., *Exp. Opin. Invest. Drugs* 5(1):79–100 (1996), Bencherif et al., *JPET* 279:1413 (1996), Lippiello et al., *JPET* 279:1422 (1996), Damaj et al., *Neuroscience* (1997), Holladay et al., *J. Med Chem* 40(28): 4169–4194 (1997), Bannon et al., *Science* 279: 77–80 (1998), PCT WO 94/08992, PCT WO 96/31475, and U.S. Pat. No. 5,583,140 to Bencherif et al., U.S. Pat. No. 5,597,919 to Dull et al., and U.S. Pat. No. 5,604,231 to Smith et al the disclosures of which are incorporated herein by reference in their entirety. Compounds of the present invention can be used as analgesics, to treat ulcerative colitis, and to treat convulsions such as those that are symtematic of epilepsy. CNS disorders which can be treated in accordance with the present invention include presenile dementia (early onset Alzheimer's disease), senile dementia (dementia of the Alzheimer's type), Parkinsonism including Parkinson's disease, Huntington's chorea, tardive dyskinesia, hyperkinesia, mania, attention deficit disorder, anxiety, dyslexia, schizophrenia and Tourette's syndrome.

The pharmaceutical composition also can include various other components as additives or adjuncts. Exemplary pharmaceutically acceptable components or adjuncts which are employed in relevant circumstances include antioxidants, free radical scavenging agents, peptides, growth factors, antibiotics, bacteriostatic agents, immunosuppressives, anticoagulants, buffering agents, anti-inflammatory agents, anti-pyretics, time release binders, anaesthetics, steroids and corticosteroids. Such components can provide additional therapeutic benefit, act to affect the therapeutic action of the pharmaceutical composition, or act towards preventing any potential side effects which may be posed as a result of administration of the pharmaceutical composition. In certain circumstances, a compound of the present invention can be employed as part of a pharmaceutical composition with other compounds intended to prevent or treat a particular disorder.

The manner in which the compounds are administered can vary. The compounds can be administered by inhalation (e.g., in the form of an aerosol either nasally or using delivery articles of the type set forth in U.S. Pat. No. 4,922,901 to Brooks et al., the disclosure of which is incorporated herein in its entirety); topically (e.g., in lotion form); orally (e.g., in liquid form within a solvent such as an aqueous or non-aqueous liquid, or within a solid carrier); intravenously (e.g., within a dextrose or saline solution); as an infusion or injection (e.g., as a suspension or as an emulsion in a pharmaceutically acceptable liquid or mixture of liquids); intrathecally; intracerebro ventricularly; or transdermally (e.g., using a transdermal patch). Although it is possible to administer the compounds in the form of a bulk active chemical, it is preferred to present each compound in the form of a pharmaceutical composition or formulation for efficient and effective administration. Exemplary methods for administering such compounds will be apparent to the skilled artisan. For example, the compounds can be administered in the form of a tablet, a hard gelatin capsule or as a time release capsule. As another example, the compounds can be delivered transdermally using the types of patch technologies available from Novartis and Alza Corporation. The administration of the pharmaceutical compositions of the present invention can be intermittent, or at a gradual, continuous, constant or controlled rate to a warm-blooded animal, (e.g., a mammal such as a mouse, rat, cat, rabbit, dog, pig, cow, or monkey); but advantageously is preferably administered to a human being. In addition, the time of day and the number of times per day that the pharmaceutical formulation is administered can vary. Administration preferably is such that the active ingredients of the pharmaceutical formulation interact with receptor sites within the body of the subject that effect the functioning of the CNS. More specifically, in treating a CNS disorder administration preferably is such so as to optimize the effect upon those relevant receptor subtypes which have an effect upon the functioning of the CNS, while minimizing the effects upon muscle-type receptor subtypes. Other suitable methods for administering the compounds of the present invention are described in U.S. Pat. No. 5,604,231 to Smith et al.

The appropriate dose of the compound is that amount effective to prevent occurrence of the symptoms of the disorder or to treat some symptoms of the disorder from which the patient suffers. By "effective amount", "therapeutic amount" or "effective dose" is meant that amount sufficient to elicit the desired pharmacological or therapeutic effects, thus resulting in effective prevention or treatment of the disorder. Thus, when treating a CNS disorder, an effective amount of compound is an amount sufficient to pass across the blood-brain barrier of the subject, to bind to relevant receptor sites in the brain of the subject, and to activatie relevant nicotinic receptor subtypes (e.g., provide neurotransmitter secretion, thus resulting in effective prevention or treatment of the disorder). Prevention of the disorder is manifested by delaying the onset of the symptoms of the disorder. Treatment of the disorder is manifested by a decrease in the symptoms associated with the disorder or an amelioration of the reoccurrence of the symptoms of the disorder.

The effective dose can vary, depending upon factors such as the condition of the patient, the severity of the symptoms of the disorder, and the manner in which the pharmaceutical composition is administered. For human patients, the effective dose of typical compounds generally requires administering the compound in an amount sufficient to activate relevant receptors to effect neurotransmitter (e.g., dopamine) release but the amount should be insufficient to induce effects on skeletal muscles and ganglia to any significant degree. The effective dose of compounds will of course differ from patient to patient but in general includes amounts starting where CNS effects or other desired therapeutic effects occur, but below the amount where muscular effects are observed.

Typically, the effective dose of compounds generally requires administering the compound in an amount of less than 1 ug/kg of patient weight. Often, the compounds of the present invention are administered in an amount from 10 ng to less than 1 ug/kg of patient weight, frequently between about 0.1 ug to less than 1 ug/kg of patient weight, and preferably between about 0.1 ug to about 0.5 ug/kg of patient weight. Compounds of the present invention can be administered in an amount of 0.3 to 0.5 ug/kg of patient weight. For compounds of the present invention that do not induce effects on muscle type nicotinic receptors at low concentrations, the effective dose is less than 50 ug/kg of patient weight; and often such compounds are administered in an amount from 0.5 ug to less than 50 ug/kg of patient weight. The foregoing effective doses typically represent that amount administered as a single dose, or as one or more doses administered over a 24 hour period.

For human patients, the effective dose of typical compounds generally requires administering the compound in an amount of at least about 1, often at least about 10, and frequently at least about 25 ug/24 hr./patient. For human patients, the effective dose of typical compounds requires administering the compound which generally does not exceed about 500, often does not exceed about 400, and frequently does not exceed about 300 ug/24 hr./patient. In addition, administration of the effective dose is such that the concentration of the compound within the plasma of the patient normally does not exceed 500 ng/ml, and frequently does not exceed 100 ng/ml.

The compounds useful according to the method of the present invention have the ability to pass across the blood-brain barrier of the patient. As such, such compounds have the ability to enter the central nervous system of the patient. The log P values of typical compounds, which are useful in carrying out the present invention are generally greater than about −0.5, often are greater than about 0, and frequently are greater than about 0.5. The log P values of such typical compounds generally are less than about 3, often are less than about 2, and frequently are less than about 1. Log P values provide a measure of the ability of a compound to pass across a diffusion barrier, such as a biological membrane. See, Hansch, et al., *J. Med. Chem.* 11:1(1968).

The compounds useful according to the method of the present invention have the ability to bind to, and in most circumstances, cause activation of, nicotinic dopaminergic receptors of the brain of the patient. As such, such compounds have the ability to express nicotinic pharmacology, and in particular, to act as nicotinic agonists. The receptor binding constants of typical compounds useful in carrying out the present invention generally exceed about 0.1 nM, often exceed about 1 nM, and frequently exceed about 10 nM. The receptor binding constants of such typical compounds generally are less than about 1 uM, often are less than about 100 nM, and frequently are less than about 50 nM. Receptor binding constants provide a measure of the ability of the compound to bind to half of the relevant receptor sites of certain brain cells of the patient. See, Cheng, et al., *Biochem. Pharmacol.* 22:3099 (1973).

The compounds useful according to the method of the present invention have the ability to demonstrate a nicotinic function by effectively activating neurotransmitter secretion from nerve ending preparations (i.e., synaptosomes). As such, such compounds have the ability to activate relevant neurons to release or secrete acetylcholine, dopamine, and other neurotransmitters. Generally, typical compounds useful in carrying out the present invention provide for the activation of dopamine secretion in amounts of at least one third, typically at least about 10 times less, frequently at least about 100 times less, and sometimes at least about 1,000 times less, than those required for activation of muscle-type nicotinic receptors. Certain compounds of the present invention can provide secretion of dopamine in an amount which is comparable to that elicited by an equal molar amount of (S)-(−)-nicotine.

The compounds of the present invention, when employed in effective amounts in accordance with the method of the present invention, are selective to certain relevant nicotinic receptors, but do not cause significant activation of receptors associated with undesirable side effects at concentrations at least greater than those required for activation of dopamine release. By this is meant that a particular dose of compound resulting in prevention and/or treatment of a CNS disorder, is essentially ineffective in eliciting activation of certain muscle-type nicotinic receptors at concentration higher than 5 times, preferably higher than 100 times, and more preferably higher than 1,000 times, than those required for activation of dopamine release. This selectivity of certain compounds of the present invention against those ganglia-type receptors responsible for cardiovascular side effects is demonstrated by a lack of the ability of those compounds to activate nicotinic function of adrenal chromaffin tissue at concentrations greater than those required for activation of dopamine release.

Compounds of the present invention, when employed in effective amounts in accordance with the method of the present invention, are effective towards providing some degree of prevention of the progression of CNS disorders, amelioration of the symptoms of CNS disorders, an amelioration to some degree of the reoccurrence of CNS disorders. However, such effective amounts of those compounds are not sufficient to elicit any appreciable side effects, as demonstrated by increased effects relating to skeletal muscle. As such, administration of certain compounds of the present invention provides a therapeutic window in which treatment of certain CNS disorders is provided, and certain side effects are avoided. That is, an effective dose of a compound of the present invention is sufficient to provide the desired effects upon the CNS, but is insufficient (i.e., is not at a high enough level) to provide undesirable side effects. Preferably, effective administration of a compound of the present invention resulting in treatment of CNS disorders occurs upon administration of less than ⅕, and often less than ⅒ that amount sufficient to cause certain side effects to any significant degree.

The following examples are provided to illustrate the present invention, and should not be construed as limiting thereof. In these examples, all parts and percentages are by weight, unless otherwise noted.

EXAMPLES

Example 1

Sample No. 1 is (3-(3-pyridyloxy)-propyl)methylamine hemigalactarate which was prepared in accordance with the following techniques:

3-Chloro-1-(3-pyridyloxy)propane

Under a nitrogen atmosphere, a solution of 3-hydroxypyridine (5.00 g, 52.58 mmol) in N,N-dimethylformamide (DMF) (55 mL) was slowly added to a cold (0–5° C.), stirring slurry of sodium hydride (2.52 g of an 80% dispersion in mineral oil, 84.0 mmol) in DMF (10 mL). The mixture was allowed to warm to ambient temperature and further stirred for 1 h. To this slurry was added 1-choro-3-iodopropane (12.90 g, 63.10 mmol), and the resulting dark-brown mixture was stirred at ambient temperature for 48 h. Cold water was added and the mixture was extracted with chloroform (4×100 mL). The combined chloroform extracts were washed with water (2×50 mL), dried ($Na_2SO_4$), filtered, and concentrated by rotary evaporation. Water (150 mL) was added, and the mixture was basified with 20% NaOH solution (5.0 mL). The alkaline solution was extracted with methyl t-butyl ether (MTBE) (5×100 mL). The combined MTBE extracts were washed with water (4×100 mL), dried ($Na_2SO_4$), filtered, and concentrated by rotary evaporation to give 4.90 g (54.3%) of an oil. $^1H$ NMR ($CDCl_3$, 300 MHz): δ8.34 (s, 1H), 8.24 (s, 1H), 7.22 (t, 2H, J=2.13 Hz), 4.18 (t, 2H, J=5.85 Hz), 3.77 (t, 2H, J=6.19 Hz), 2.27 (p, 2H, J=6.03 Hz). $^{13}C$ NMR ($CDCl_3$, 75 MHz):

δ154.99, 142.38, 138.07, 123.93, 121.09, 64.60, 41.22, 32.11. EI-MS: m/z (relative intensity) 171 ($M^+$, 27.25%), 136 (4.66%), 95 (100.00%), 78 (17.98%), 41 (37.74%), 39 (34.23%).

(3-(3-Pyridyloxy)propyl)methylamine

The 3-chloro-1-(3-pyridyloxy)propane (4.90 g, 28.55 mmol) was dissolved in methanol (60 mL) and added to a 40 wt % solution of methylamine (60 mL) in a heavy-walled pressure-tube apparatus. The tube was sealed and the mixture was stirred and heated at 80° C. for 15 h. After cooling, the mixture was concentrated by rotary evaporation, a saturated NaCl solution (25 mL) was added, and the mixture was basified with 20% NaOH solution (5.0 mL). The mixture was extracted with chloroform (4×30 mL). The combined chloroform extracts were dried ($Na_2SO_4$), filtered, and concentrated by rotary evaporation to give 3.64 g of a brown oil. The product was purified by column chromatography on silica gel (100 g) eluting with chloroform-methanol-triethylamine (70:30:2.5, v/v/v). Selected fractions containing the product ($R_f$ 0.30) were combined and concentrated by rotary evaporation. The resulting residue was dissolved in chloroform (15 mL), dried ($Na_2SO_4$), filtered, and concentrated by rotary evaporation to give 1.92 g (40.4%) of a brown oil. $^1$H NMR ($CDCl_3$, 300 MHz): δ8.31 (dd, 1H, J=2.39, 1.44 Hz), 8.20 (dd, 1H, J=3.88, 2.29 Hz), 7.14 (m, 2H, J=3.90, 1.11 Hz), 4.09 (t, 2H, J=6.22 Hz), 2.78 (t, 2H, J=6.80 Hz), 2.46 (s, 3H), 1.99 (p, 2H, J=6.54 Hz), 1.59 (br, s, 1H). $^{13}$C NMR ($CDCl_3$, 75 MHz): δ155.16, 142.08, 138.09, 123.84, 121.05, 66.59, 48.78, 36.53, 29.44. EI-MS: m/z (relative intensity) 166 ($M^+$, 10.08%), 123 (41.85%), 95 (100.00%), 70 (45.84%), 44 (89.75%), 39 (41.62%).

(3-(3-Pyridyloxy)propyl)methylamine Hemigalactarate

To a solution of (3-(3-pyridyloxy)propyl)methylamine (800.0 mg, 4.81 mmol) in ethanol (12 mL) was added galactaric acid (505.7 mg, 2.41 mmol). Water (2.5 mL) was added dropwise, while gently warming the light-yellow solution. To remove some white, insoluble solids, the warm solution was filtered through a glass wool plug, washing the filter plug with a warm solution of ethanol-water (4:1, v/v) (4 mL). The filtrate was diluted with ethanol (18 mL), producing a white precipitate. The mixture was allowed to cool to ambient temperature and was further cooled at 5° C. for 15 h. The precipitate was filtered, washed with ethanol (6 mL), vacuum dried at 45° C. for 10 h, followed by further vacuum drying at ambient temperature for 48 h to give 994.4 mg (76.1%) of an off-white, crystalline powder, mp 161–165.5° C. FT-IR (powder): 3000 (s, br, O—H of COOH), 3100–2800 (s, br, C—H), 3600–2300 (s, br, C—OH), 1585 (s, $COO^-$), 1422 (s, $COO^-$), 1365 (s, $COO^-$), 1272 (s, C—O, mixed ether), 1230 (m), 1106 (s, C—O, mixed ether), 1045 (s), 808 (w, 3-subst. pyridine), 770 (w), 707 (m, 3-subst. pyridine), 665 (w), 635 (w) $cm^{-1}$. $^1$H NMR ($D_2O$, 300 MHz): δ8.27 (s, 1H), 8.19 (d, 1H, J=3.27 Hz), 7.51–7.41 (m, 2H), 4.27 (s, 1H), 4.25 (t, 2H, J=5.70 Hz), 3.97 (s, 1H), 3.30 (t,2H, J=7.18 Hz), 2.78 (s, 3H), 2.24 (p, 2H, J=7.18 Hz). $^{13}$C NMR ($D_2O$, 75 MHz): δ182.33, 157.61, 144.41, 139.76, 127.76, 125.60, 74.58, 74.28, 68.73, 49.82, 35.87, 28.17. EI-MS: m/z (relative intensity) 166 ($M^+$, 1.88%), 123 (3.81%), 95 (24.34%), 78 (3.91%), 44 (100.00%).

Calcd. for $C_9H_{14}N_2O \cdot 0.5\ C_6H_{10}O_8$: C, 53.12; H, 7.06; N, 10.33. Found: C, 53.06; H, 7.08; N, 10.27.

Example 2

Sample No. 2 is (3-(5-bromo(3-pyridyloxy))propyl)methylamine hemigalactarate which was prepared in accordance with the following techniques:

5-Bromo-3-hydroxypyridine

5-Bromo-3-hydroxypyridine was prepared from 2-furfurylamine according to the procedure described in U.S. Pat. No. 4,192,946 to Clauson-Kaas et al.

3-Bromo-5-(3-chloropropoxy)pyridine

Under a nitrogen atmosphere, a solution of 5-bromo-3-hydroxypyridine (1.90 g, 10.92 mmol) in DMF (10 mL) was slowly added over 10 min to a cold (0–5° C.), stirring slurry of sodium hydride (0.52 g of an 80% dispersion in mineral oil, 17.47 mmol) in DMF (14 mL). The mixture was allowed to warm to ambient temperature and further stirred for 1 h. To this slurry was added dropwise over 5 min 1-choro-3-iodopropane (2.68 g, 13.10 mmol), and the resulting dark-brown mixture was stirred at ambient temperature for 48 h. Cold water (30 mL) was carefully added, followed by saturated NaCl solution (20 mL). The resulting mixture was extracted with ether (5×25 mL). The combined ether extracts were dried ($Na_2SO_4$), filtered, and concentrated by rotary evaporation producing a dark-brown oil (4.07 g). The product was used in the next step without further purification. EI-MS: m/z (relative intensity) 251 ($M^+$, 31.89%), 249 ($M^+$, 23.99%), 175 (65.68%), 173 (67.42%), 94 (37.06%), 41 (100.00%).

(3-(5-Bromo(3-pyridyloxy))propyl)methylamine

Crude 3-bromo-5-(3-chloropropoxy)pyridine (4.07 g) from the previous step was dissolved in $CH_3OH$ (28 mL) and added to a 40 wt % solution of methylamine (35 mL) in a heavy-walled pressure-tube apparatus. The tube was sealed and the mixture was stirred and heated at 102° C. for 4 h. After cooling, the solution was concentrated by rotary evaporation, a saturated NaCl solution (15 mL) was added, and the mixture was basified with 10% NaOH solution (5 mL). The mixture was extracted with $CHCl_3$ (4×30 mL). The combined $CHCl_3$ extracts were dried ($Na_2SO_4$), filtered, and concentrated by rotary evaporation to give 2.07 g of a brown oil. The product was purified by column chromatography on silica gel (100 g) eluting with $CHCL_3$—$CH_3OH$ (9:1, v/v) to remove impurities, followed by $CHCL_3$—$CH_3OH$—Et3N (75:25:2, v/v/v) to collect the product. Selected fractions containing the product ($R_f$ 0.13) were combined and concentrated by rotary evaporation. The resulting brown oil was dissolved in $CHCl_3$ (25 mL), dried ($Na_2SO_4$), filtered, and concentrated by rotary evaporation to give 0.79 g (29.5% based upon 5-bromo-3-hydroxypyridine) of an amber-brown oil, which tended to crystallize as light amber crystals. $^1$H NMR ($CDCl_3$, 300 MHz): δ8.27 (d, 1H, J=1.85 Hz), 8.24 (d, 1H, J=2.48 Hz), 7.38 (dd, 1H, J=1.91, 1.91 Hz), 4.09 (t, 2H, J=6.22 Hz), 2.78 (t, 2H, J=6.84Hz), 2.47 (s, 3H), 1.99 (p,2H, J=6.56 Hz), 1.53 (br s, 1H).

(3-(5-Bromo(3-pyridyloxy))propyl)methylamine Hemigalactarate

To a solution of (3-(5-bromo(3-pyridyloxy))propyl) methylamine (0.790 g, 3.22 mmol) in ethanol (12 mL) was added galactaric acid (339.0 mg, 1.61 mmol). Water (3.4 mL) was added dropwise, while warming the light-yellow solution to near reflux. To remove some white, insoluble crystals, the warm solution was filtered through a glass wool plug, washing the filter plug with a warm solution of ethanol-water (4:1, v/v) (3.8 mL). The filtrate was diluted with ethanol (18 mL), producing a light-beige precipitate. The mixture was allowed to cool to ambient temperature and was further cooled at 5° C. for 48 h. The precipitate was filtered, washed with ethanol (5 mL), vacuum dried at 40 C. for 24 h to give 983.3 mg (68.8%) of a glassy, beige powder, mp 166–173.5° C. $^1$H NMR ($D_2O$, 300 MHz): δ8.25 (d, 1H, J=1.78 Hz), 8.20 (d, 1H, J=2.54 Hz), 7.67 (dd, 1H, J=1.81, 1.81 Hz), 4.28 (s, 1H), 4.22 (t, 2H, J=5.70 Hz), 3.98 (s, 1H), 3.29 (t, 2H, J=7.21 Hz 2.79 (s, 3H), 2.25 (p, 2H, J=6.60 Hz). $^{13}$C NMR (D$_2$O, 75 MHz): δ188.14, 182.32, 157.90, 145.18, 138.61, 128.05, 123.26, 74.58, 74.28, 69.05, 49.67, 35.86, 28.08. EI-MS: m/z (relative intensity) 246 (M$^+$, 1.55%), 244 (M$^+$, 1.54%), 175 (4.98%), 173 (5.10%), 118 (2.59%), 116 (2.66%), 70 (5.67%), 44 (100.00%), (9.89%). ES-MS: m/z 247, 245 [M+H]$^+$.

Calcd. for C$_9$H$_{13}$N$_2$Br 0.5 C$_6$H$_{10}$O$_8$: C, 41.16; H, 5.18; N, 8.00; Br, 22.82. Found: C, 41.20; H, 5.20; N, 7.88; Br, 22.67.

Example 3

Determination of Log P Value

Log P values, which have been used to assess the relative abilities of compounds to pass across the blood-brain barrier (Hansch, et al., *J. Med. Chem.* ii:1(1968)), were calculated according using the Cerius$^2$ software package Version 3.0 by Molecular Simulations; Inc.

Sample No. 1 exhibits a log P of 0.562 and Sample No. 2 exhibits a log P of 0.662, and such favorable log P values indicate that the compounds have the capability of passing the blood-brain barrier.

Example 4

Determination of Binding to Relevant Receptor Sites

Binding of the compounds to relevant receptor sites was determined in accordance with the techniques described in U.S. Pat. No. 5,597,919 to Dull et al. Inhibition constants (Ki values), reported in nM, were calculated from the IC$_{50}$ values using the method of Cheng et al., *Biochem, Pharmacol.* 22:3099 (1973).

Sample No. 1 exhibits a Ki of 13 nM and Sample No. 2 exhibits a Ki of 44 nM. The low binding constants indicate that the compounds exhibit good high affinity binding to certain CNS nicotinic receptors.

Example 5

Determination of Dopamine Release

Dopamine release was measured using the techniques described in U.S. Pat. No. 5,597,919 to Dull et al. Release is expressed as a percentage of release obtained with a concentration of (S)-(-)-nicotine resulting in maximal effects. Reported EC$_{50}$ values are expressed in nM, and E$_{max}$ values represent the amount released relative to (S)-(-)-nicotine on a percentage basis.

Sample No. 1 exhibits an EC$_{50}$ value of 369 nM and an E$_{max}$ value of 96%, indicating that the compound effectively induces neurotransmitter release thereby exhibiting known nicotinic pharmacology.

Example 6

Determination of Rubidium Ion Release

Rubidium release was measured using the techniques described in Bencherif et al., *JPET,* 279: 1413–1421 (1996). Reported EC$_{50}$ values are expressed in nM, and E$_{max}$ values represent the amount of rubidium ion released relative to 300 uM tetramethylammonium ion, on a percentage basis.

Sample No. 1 exhibits an EC$_{50}$ value of 960 nM and an E$_{max}$value of 83%, indicating that the compound effectively induces activation of CNS nicotinic receptors.

Example 7

Determination of Interaction with Muscle Receptors

The determination of the interaction of the compounds with muscle receptors was carried out in accordance with the techniques described in U.S. Pat. No. 5,597,919 to Dull et al. The maximal activation for individual compounds (E$_{max}$) was determined as a percentage of the maximal activation induced by (S)-(-)-nicotine. Reported E$_{max}$ values represent the amount released relative to (S)-(-)-nicotine on a percentage basis.

Sample No. 1 exhibits an E$_{max}$ of 0% at muscle-type receptors, indicating that the compound does not induce activation of muscle-type receptors. The compound has the capability to activate human CNS receptors without activating muscle-type nicotinic acetylcholine receptors. Thus, there is provided a therapeutic window for utilization in the treatment of CNS disorders. That is, at certain levels the compound shows CNS effects to a significant degree but do not show undesirable muscle effects to any significant degree. The compound begins to cause muscle effects only when employed in amounts of many times those required to activate dopamine release.

Example 8

Determination of Interaction with Ganglion Receptors

The determination of the interaction of the compounds with ganglionic receptors was carried out in accordance with the techniques described in U.S. Pat. No. 5,597,919 to Dull et al. The maximal activation for individual compounds (E$_{max}$) was determined as a percentage of the maximal activation induced by (S)-(-)-nicotine. Reported E$_{max}$ values represent the amount released relative to (S)-(-)-nicotine on a percentage basis.

Sample No. 1 exhibits an E$_{max}$ of 93% at ganglionic-type receptors.

Example 9

In Vivo Evaluation

A Gemini Avoidance System (San Diego Instruments) were used to evaluate animals in a passive avoidance experiment. During the period of habituation, laboratory rats received a subcutaneous injection of saline. On the acquisition day, each rat received a subcutaneous injection of 0.5 umol/kg scopolamine (or saline in the. case of the vehicle control group) 30 minutes prior to being placed in the chambers. Five minutes following scopolamine injection, (or 25 minutes before being placed in the chamber), each rat was administered a subcutaneous injection with one of four doses of Sample No. 1. Thirty minutes following the scopolamine or vehicle injection, each rat was placed in the brightly illuminated chamber, facing away from the sliding door. After 10 seconds, the door separating the chambers opened allowing access to the dark chamber. The time to enter the dark chamber was measured. Immediately upon entering the dark chamber, the rat received a mild foot shock (0.5 mAmp) for 2 seconds. Twenty four hours following training, each rat was placed in the light chamber facing away from the sliding door. Thirty seconds later the door was opened and each rat was allowed to enter the dark chamber. Upon entering the dark chamber the sliding door was closed and the rat was removed from the apparatus (no shock was administered). If the rat did not enter the dark chamber within 300 seconds, a ceiling score of 300 seconds was recorded for that rat, and the rat was removed from the apparatus and returned to its home cage. Statistical differences in latencies (latency during acquisition and retention trials) were analyzed by Kruskal-Wallis one-way analysis of variance on ranks followed by the either of two-tailed Mann-Whitney U-test or Newman-Keuls analog test if values of p less than 0.05 were obtained. Sample No. 1 at concentrations of 0.3 to 3 umol/kg resulted in significant reversal of scopolamine induced amnesia in the step-through passive avoidance paradigm using laboratory rats. Thus, the compound has potential cognition enhancing effects, an end-point relevant to certain CNS disorders.

The foregoing is illustrative of the present invention and is not to be construed as limiting thereof. The invention is defined by the following claims, with equivalents of the claims to be included therein.

That which is claimed is:

1. A method for treating a central nervous system disorder comprising administering to a subject in need thereof, an effective amount of a compound of the formula:

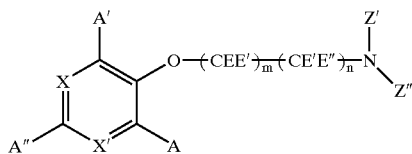

where X is selected from the group consisting of C—H, C—F, C—Cl, C—Br, C—I, C—R', C—NR'R", C—CF$_3$, C—OH, C—CN, C—NO$_2$, C—C$_2$R', C—SH, C—SCH$_3$, C—N$_3$, C—SO$_2$CH$_3$, C—OR', C—SR', C—C(=O)NR'R", C—NR'C(=O)R', C—C(=O)R', C—C(=O)OR', C(CH$_2$)$_q$OR', C—OC(=O)R', COC(=O)NR'R" and C—NR'C(=O)OR' wherein R' and R" are individually hydrogen, lower alkyl, an aromatic group containing species or a substituent aromatic group; and q is an integer from 1 to 6; X' is nitrogen; m is an integer and n is an integer such that the sum of m plus n is 1, 2, 3, 4, 5, 6, 7, or 8; E, E', E" and E''' individually are hydrogen or lower alkyl; Z' and Z" individually are hydrogen or lower alkyl; A' and A" are selected from the group consisting of H, C(CH2)$_q$OR', R', NR'R", CF$_3$, OH, CN, NO$_2$, C$_2$R', SH, SCH$_3$, N$_3$, SO$_2$CH$_3$, OR', SR', C(=O)NR'R", NR'C(=O)R', C(=O)R', C(=O)OR', OC(=O)R', OC(=O)NR'R" and NR'C(=O)OR', F, Br, Cl and I; wherein R', R" and q are as defined previously; and A is selected from the group consisting of hydrogen, lower alkyl, F, Br, Cl, and I.

2. The method of claim 1, whereby A is hydrogen or methyl.

3. The method of claim 1, whereby Z' and Z" are hydrogen.

4. The method of claim 1, whereby one of Z' and Z" is lower alkyl and the other hydrogen.

5. The method of claim 1, whereby one of Z' and Z" is methyl and the other hydrogen.

6. The method of claim 1, whereby Z' and Z" are both lower alkyl.

7. The method of claim 1, whereby Z' and Z" are both methyl.

8. The method of claim 1, whereby X is selected from the group consisting of CF, CBr, CCl and Cl.

9. The method of claim 1, whereby X is COR' and R' is lower alkyl.

10. The method of claim 9, whereby R' is methyl, ethyl or isopropyl.

11. The method of claim 1, whereby E' and E" are methyl.

12. The method of claim 1, whereby m plus n is 2 or 3.

13. The method of claim 1, whereby the compound is (3-(3-pyridyloxy)propyl)methylamine.

14. The method of claim 1, whereby the compound is (3-(5-bromo(3-pyridyloxy))-propyl)methylamine.

15. A compound of the formula:

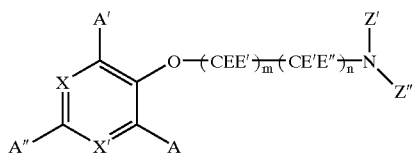

where X is selected from the group consisting of C—H, C—F, C—Cl, C—Br, C—I, C—R', C—NR'R", C—CF$_3$, C—OH, C—CN, C—NO$_2$, C—C$_2$R', C—SH, C—SCH$_3$, C—N$_3$, C—SO$_2$CH$_3$, C—OR', C—SR', C—C(=O)NR'R", C—NR'C(=O)R', C—C(=O)R', C—C(=O)OR', C(CH$_2$)$_q$OR', C—OC(=O)R', COC(=O)NR'R" and C—NR'C(=O)OR' wherein R' and R" are individually hydrogen, lower alkyl, an aromatic group containing species or a substituent aromatic group; and q is an integer from 1 to 6; X' is nitrogen; m is an integer and n is an integer such that the sum of m plus n is 1, 2, 3, 4, 5, 6, 7, or 8; E, E', E" and E''' individually are hydrogen or lower alkyl; Z' and Z" individually are hydrogen or lower alkyl; A' and A" are selected from the group consisting of H, C(CH2)$_q$OR', R', NR'R", CF$_3$, OH, CN, NO$_2$, C$_2$R', SH, SCH$_3$, N$_3$, SO$_2$CH$_3$, OR', SR', C(=O)NR'R", NR'C(=O)R', C(=O)R', C(=O)OR', OC(=O)R', OC(=O)NR'R" and NR'C(=O)OR', F, Br, Cl and I; wherein R', R" and q are as defined previously; and A is selected from the group consisting of hydrogen, lower alkyl, F, Br, Cl, and I.

16. The compound of claim 15, whereby A is hydrogen or methyl.

17. The compound of claim 15, whereby Z' and Z" are hydrogen.

18. The compound of claim 15, whereby one of Z' and Z" is lower alkyl and the other hydrogen.

19. The compound of claim 15, whereby one of Z' and Z" is methyl and the other hydrogen.

20. The compound of claim 15, whereby Z' and Z" are both lower alkyl.

21. The compound of claim 15, whereby Z' and Z" are both methyl.

22. The compound of claim 15, whereby X is selected from the group consisting of CF, CBr, CCl and Cl.

23. The compound of claim 15, whereby X is COR' and R' is lower alkyl.

24. The compound of claim 23, whereby R' is methyl, ethyl or isopropyl.

25. The compound of claim 15, whereby E' and E" are methyl.

26. The compound of claim 15, whereby m plus n is 2 or 3.

27. The compound of claim 15, (3-(3-pyridyloxy)propyl)methylamine.

28. The compound of claim 15, (3-(5-bromo(3-pyridyloxy))-propyl)methylamine.

29. A pharmaceutical composition incorporating an effective amount of compound of the formula:

where X is selected from the group consisting of C—H, C—Cl, C—Br, C—I, C—R', C—NR'R", C—CF$_3$, C—OH, C—CN, C—NO$_2$, C—C$_2$R', C—SH, C—SCH$_3$, C—N$_3$, C—SO$_2$CH$_3$, C—OR', C—SR', C—C(=O)NR'R", C—NR'C(=O)R', C—C(=O)R', C—C(=O)OR', C(CH$_2$)$_q$OR', C—OC(=O)R', COC(=O)NR'R" and C—NR' C(=O)OR' wherein R' and R" are individually hydrogen, lower alkyl, an aromatic group containing species or a substituent aromatic group; and q is an integer from 1 to 6; X' is nitrogen; m is an integer and n is an integer such that the sum of m plus n is 1, 2, 3, 4, 5, 6, 7, or 8; E, E', E" and E'" individually are hydrogen or lower alkyl; Z' and Z" individually are hydrogen or lower alkyl; A'and A" are selected from the group consisting of H, C(CH$_2$)$_q$OR', R', NR'R", CF$_3$, OH, CN, NO$_2$, C$_2$R', SH, SCH$_3$, N$_3$, SO$_2$CH$_3$, OR', SR', C(=O)NR'R", NR'C(=O)R', C(=O)R', C(=O)OR', OC(=O)R', OC(=O)NR'R" and NR'C(=O)OR', F, Br, Cl and I; wherein R', R" and q are as defined previously; and A is selected from the group consisting of hydrogen, lower alkyl, F, Br, Cl, and I.

30. The pharmaceutical composition of claim 29, wherein A is hydrogen or methyl.

31. The pharmaceutical composition of claim 29, wherein Z' and Z" are hydrogen.

32. The of pharmaceutical composition of claim 29, wherein one of Z' and Z" is lower alkyl and the other hydrogen.

33. The pharmaceutical composition of claim 29, wherein one of Z' and Z" is methyl and the other hydrogen.

34. The pharmaceutical composition of claim 29, wherein Z' and Z" are both lower alkyl.

35. The pharmaceutical composition of claim 29, wherein Z' and Z" are both methyl.

36. The pharmaceutical composition of claim 29, wherein X is selected from the group consisting of CF, CBr, CCl and Cl.

37. The pharmaceutical composition of claim 29, wherein X is COR' and R' is lower alkyl.

38. The pharmaceutical composition of claim 37, wherein R' is methyl, ethyl or isopropyl.

39. The pharmaceutical composition of claim 29, wherein E' and E" are methyl.

40. The pharmaceutical composition of claim 29, wherein m plus n is 2 or 3.

41. The pharmaceutical composition of claim 29, wherein the compound is (3-(3-pyridyloxy)propyl)methylamine.

42. The pharmaceutical composition of claim 29, wherein the compound is (3-(5-bromo(3-pyridyloxy))-propyl) methylamine.

* * * * *